United States Patent
Hong et al.

(10) Patent No.: US 10,115,034 B2
(45) Date of Patent: Oct. 30, 2018

(54) METHOD AND SYSTEM FOR PROJECTING IMAGE WITH DIFFERING EXPOSURE TIMES

(71) Applicants: LIFE TECHNOLOGIES HOLDINGS PTE LIMITED, Carlsbad, CA (US); PIERCE BIOTECHNOLOGY, INC., Carlsbad, CA (US)

(72) Inventors: Suk Hong, Roscoe, IL (US); Nikki Jarrett, Roscoe, IL (US); Eric Hommema, Roscoe, IL (US); Jason Aravich, Pittsburgh, PA (US); Yanpeng Cao, Singapore (SG); Benyong Shi, Singapore (SG); Kok Siong Teo, Singapore (SG)

(73) Assignees: LIFE TECHNOLOGIES HOLDINGS PTE LIMITED, Carlsbad, CA (US); PIERCE BIOTECHNOLOGY, INC., Carlsbad, CA (US)

( * ) Notice: Subject to any disclaimer, the term of this patent is extended or adjusted under 35 U.S.C. 154(b) by 194 days.

(21) Appl. No.: 15/294,667

(22) Filed: Oct. 14, 2016

(65) Prior Publication Data

US 2017/0103279 A1 Apr. 13, 2017

Related U.S. Application Data

(63) Continuation-in-part of application No. 14/264,150, filed on Apr. 29, 2014.

(60) Provisional application No. 61/818,107, filed on May 1, 2013.

(51) Int. Cl.
| | | |
|---|---|---|
| G06K 9/46 | (2006.01) | |
| H04N 5/235 | (2006.01) | |
| G06T 7/00 | (2017.01) | |

(52) U.S. Cl.
CPC ......... *G06K 9/4647* (2013.01); *G06T 7/0002* (2013.01); *H04N 5/2351* (2013.01); *H04N 5/2353* (2013.01); *G06T 2207/10144* (2013.01); *G06T 2207/30072* (2013.01); *G06T 2207/30168* (2013.01)

(58) Field of Classification Search
CPC ..... G06K 9/4647; H04N 5/23; G06T 2207/30
See application file for complete search history.

(56) References Cited

U.S. PATENT DOCUMENTS

| | | |
|---|---|---|
| 5,585,942 A | 12/1996 | Kondo |
| 5,734,426 A | 3/1998 | Dong |
| 5,751,352 A | 5/1998 | Ogawa |
| 6,665,010 B1 | 12/2003 | Morris et al. |

(Continued)

*Primary Examiner* — Zhubing Ren

(57) ABSTRACT

Systems and methods generate a projected image at an optimal exposure time. Images are captured different exposure times. Pixels that satisfy an intensity threshold percentage for each image are selected. The intensity values of the selected pixels are then evaluated to determine whether the selected pixels are distributed above a lower intensity threshold and below an upper intensity threshold. The linear relationship is projected to determine an optimal exposure time that has an optimal exposure time duration that exceeds each exposure time duration associated with each of the captured images when the linear relationship exists between each of the captured images. A projected image associated with the optimal exposure time is generated from one or more of the captured images.

16 Claims, 13 Drawing Sheets

(56) References Cited

U.S. PATENT DOCUMENTS

| | | |
|---|---|---|
| 7,292,280 B2 | 11/2007 | Yamazaki et al. |
| 7,304,683 B2 | 12/2007 | Ricardo |
| 7,646,407 B2 | 1/2010 | Fossum et al. |
| 7,728,897 B2 | 6/2010 | Milkov et al. |
| 7,897,902 B2 | 3/2011 | Katzir et al. |
| 8,040,394 B2 | 10/2011 | Fossum et al. |
| 2005/0104615 A1 | 5/2005 | Kim |
| 2007/0237514 A1 | 10/2007 | Pillman et al. |
| 2010/0136549 A1* | 6/2010 | Christiansen ......... G06T 7/0012 435/6.1 |
| 2010/0177221 A1 | 7/2010 | Lee |
| 2010/0321484 A1* | 12/2010 | Kishima ............... G02B 21/365 348/79 |
| 2011/0013064 A1 | 1/2011 | Lahav et al. |
| 2011/0317259 A1* | 12/2011 | Tanabe ............... G02B 21/0032 359/383 |
| 2012/0276555 A1 | 11/2012 | Kuhn et al. |

* cited by examiner

METHOD AND SYSTEM FOR PROJECTING IMAGE WITH DIFFERING EXPOSURE TIMES

The present application is a Continuation-in-Part (CIP) of co-pending U.S. patent application Ser. No. 14/264,150, filed Apr. 29, 2014, which claims the filing benefit of U.S. Provisional Application Ser. No. 61/818,107, filed May 1, 2013, each disclosure of which is hereby incorporated herein by reference in its entirety.

FIELD OF THE INVENTION

The present invention relates generally to pixel optimization, and more particularly, to projecting an image with different exposure times to determine the exposure time for pixel optimization.

BACKGROUND OF THE INVENTION

Life science researchers routinely obtain images of mixtures of macromolecules, such as DNA, RNA and proteins, and their fragments, from stained gel electrophoresis samples and Western blots. The images are then captured and analyzed to obtain data.

In order to separate the complex mixtures using electrophoresis, several samples containing the mixture are applied to separate, spaced apart locations on the electrophoresis gel. An electrical current is then applied to the gel, which causes the individual samples to migrate through the gel within their prescribed lane or track, thereby generating an invisible lane on the gel. The complex mixture is then separated by size, i.e., molecular weight, and net charge in the gel matrix. The larger, higher molecular weight with low net charge molecules remain relatively nearer the place of sample loading on the gel or membrane. The smaller, lower molecular weight molecules with high net charge migrate farther from the sample loading place of the gel or membrane. Each individual segregation of sample is then identified as a band. The gel can then be stained for total sample visualization, or transferred to a membrane for visualization of a specific target of interest by blotting (Western blotting in the case of proteins, Southern blotting in the case of DNA, and Northern blotting in the case of RNA). The researcher then images the gel, membrane or blot, collectively termed a substrate or object, to analyze the target(s) of interest for amount, relative or absolute, purity, and molecular weight. Such analysis requires detection and identification of the lanes and bands in the image.

The images of the object are typically acquired using one or more visualization means, such as ultra violet illumination, white light illumination, fluorescence, or chemiluminescence.

Finding proper exposure time is an important factor affecting image quality and it is important for successful, accurate pixel intensity measurement on the acquired image. Various auto exposure methods have been developed, but those methods are either complex, inaccurate and/or disregard user input. Optimal exposure time for image capture is not always dependent on pixel intensity of the entire image or any particular region of the image. In some cases, the user/operator can best define which object(s) on the captured image should be the target for optimal exposure determination.

Images of the substrate, or of other objects, can be captured by any of a wide variety of structures or devices, but in one case takes the form of an imaging device or image capture device utilizing/comprising a CCD (Charge Coupled Device), but can also be used with autoradiography, scanners, CMOS (Complementary Metal Oxide Semiconductor) imagers, phosphor imagers, and others. In the case of the CCD, such a system utilizes an array of light-sensitive optical elements, such as pixels or other light sensing units. The pixels are configured such that when light (photons) are detected by the pixels, each pixel provides an output in the form of an electrical signal that is proportional or related to the intensity of the detected light (photons). Multiple pixels or arrays of pixels can also be combined together using the well-known binning technique, and in this case each group of binned pixels can be considered a single pixel.

Each pixel has a limited capacity for maximum light exposure, also known as its saturation point. If too many pixels reach their saturation point for a given image, the image is considered over-exposed. In contrast, if too many of the pixels receive insufficient light, the image lacks sufficient contrast and is considered under-exposed. Thus, when capturing images it is helpful to determine the optimal exposure time so that data from the image can be accurately captured. Use of the optimal exposure time maximizes the dynamic range of the pixel intensities in the image, and minimizes the number of pixels that are saturated.

In previous systems, in order to determine the proper exposure time for image acquisition, a trial-and-error image acquisition process or a complex, inaccurate automatic exposure method was utilized. The user/operator would need to carry out multiple image acquisitions with differing exposure times, compare the images, and make estimates as to the best exposure time. However this process is labor-intensive and also takes up usage of the imaging equipment that would otherwise be put to productive use.

SUMMARY OF THE INVENTION

The present invention overcomes the foregoing and other shortcomings and drawbacks of known pump monitoring devices for use in fluid circuits. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, a computer implemented method generates a projected image at an optimal exposure time. A plurality of images is captured with each image captured at a different exposure time. Each image of the plurality of images is assessed and pixels are selected that have intensity values that satisfy an intensity threshold percentage for each image. The intensity threshold percentage is a percentage of pixels included in the image with each pixel included in the percentage of pixels having an intensity value that is higher than an intensity value for each pixel that is excluded from the percentage of pixels. The intensity values are evaluated as to whether the selected pixels are distributed above a lower intensity threshold and below an upper intensity threshold. Whether a linear relationship exists of the intensity values between each of the captured images with the intensity values of the selected pixels that are above the lower intensity threshold and below the upper intensity threshold between each of the captured images is determined. A linear relationship is projected to determine an optimal exposure time that has an exposure time duration that exceeds each exposure time duration associated with each of the captured images when the linear relationship exists between each of the captured images. The optimal exposure time is based upon a pixel intensity saturation level threshold. A projected image associated with the optimal exposure time is generated from one or more of the captured images.

According to another aspect of the present invention, a system for generating a projected image with an optimal exposure time includes an image capturing device. The image capturing device is configured to capture a plurality of images with each image captured at a different exposure time. The system also includes at least one processor with a memory coupled with the processor. The memory includes instructions, that when executed by the processor cause the processor to assess each image of the plurality of images and select pixels that have intensity values that satisfy an intensity threshold percentage for each image. The intensity threshold percentage is a percentage of pixels included in the image with each pixel included in the percentage of pixels having an intensity value that is higher than an intensity value for each pixel that is excluded from the percentage of pixels. The processor is configured to evaluate whether the intensity values of the selected pixels are distributed over a lower intensity threshold and below an upper intensity threshold. The processor is configured to determine whether a linear relationship exists of the intensity values between each of the captured images with the intensity values of the selected pixels that are above the lower intensity threshold and below the upper intensity threshold between each of the captured images. The processor is configured to determine an optimal exposure time that has an exposure time duration that exceeds each exposure time duration associated with each of the captured images when the linear relationship exists between each of the captured images. The optimal exposure time is based upon a pixel intensity saturation level threshold. The processor is configured to generate a projected image associated with the optimal exposure time from one or more of the captured images.

The above and other objectives and advantages of the present invention shall be made apparent from the accompanying drawings and description thereof.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiments given below, serve to explain the principles of the invention.

DETAILED DESCRIPTION OF THE INVENTION

Figure 1:
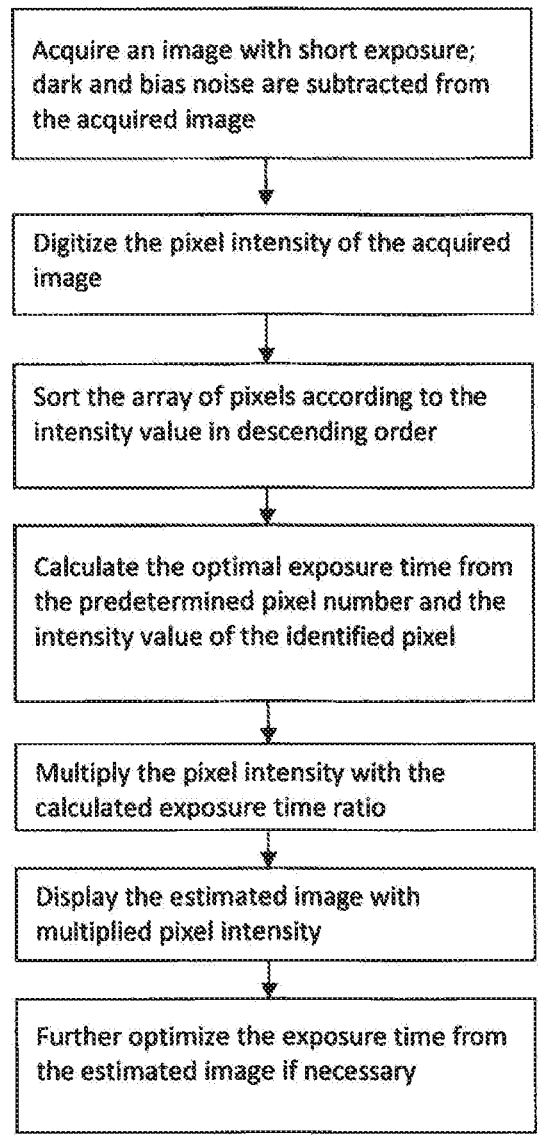
FIG. 1 is a flowchart of an exemplary process for determining the optimal exposure time for image acquisition based upon a single image acquisition according to one embodiment of the invention.

In the Detailed Description herein, references to "one embodiment", "an embodiment", an "example embodiment", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with an embodiment of the present invention, Applicants submit that it may be within the knowledge of one skilled in the art to affect such feature, structure, or characteristic in connection with other embodiments of the present invention whether or not explicitly described.

Embodiments of the present invention may be implemented in hardware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

For purposes of this discussion, each of the various components discussed can be considered a module, and the term "module" shall be understood to include at least one software, firmware, and hardware (such as one or more circuit, microchip, or device, or any combination thereof), and/or any combination thereof. In addition, it will be understood that each module can include one, or more than one, component within an actual device, and each component that forms a part of the described module can function either cooperatively or independently of any other component forming a part of the module. Conversely, multiple modules described herein can represent a single component within an actual device. Further components within a module can be in a single device or distributed among multiple devices in a wired or wireless manner.

The following detailed description refers to the accompanying drawings that illustrate exemplary embodiments of the present invention. Other embodiments are possible, and modifications can be made to the embodiments within the spirit and scope of this description. Those skilled in the art with access to the teachings provided herein will recognize additional modifications, applications, and embodiments within the scope thereof and additional fields in which embodiments would be of significant utility. Therefore, the detailed description is not meant to limit the present invention to the embodiments described below.

Thus, in one embodiment the present invention provides a system and method for providing, and/or enabling a user/operator to determine the optimal exposure time for image acquisition based upon only a single image acquisition. With reference to FIG. 1, a test or preliminary image of the substrate or object is first obtained under a test, or first, exposure time. The timing/value of the test exposure time can vary as needed, and according to the specific equipment and nature of image expected to be acquired. However, the test exposure time in many cases is shorter than the normal or expected full or optimal exposure time. In one case, for example, the test exposure time is between about 10 milliseconds and about 10 minutes, or in another case between about 1 second and about 60 seconds, or more particularly between about 5 seconds and about 25 seconds, or in one case less than about 60 minutes, or in another case less than about 1 minute.

After the image (test image) at the test exposure time is acquired, noise subtraction algorithms (including accounting for dark noise, bias noise, flat field, etc.) are applied to the data/image in a well-known manner. The signal intensity, or output, of each pixel can then be arranged/ordered. The system then analyzes the number of pixels that exceed a threshold value (and/or are projected to exceed a threshold value), and uses that number to determine the optimal exposure time.

By way of example, in a 16 bit image system, the output of each pixel can be an integer ranging from 0 to 65,535. Of course, 8 bit, 32 bit, gray or color or other imaging systems can be utilized, and the output values of each pixel can therefore vary widely. The system can then analyze the number of pixels that are at saturation value (e.g. at 65,535 for a 16 bit image) or at some value close to saturation (e.g. 90% of saturation in one case, at a value at or exceeding 58,982), or some other threshold value. The system will have pre-programmed into it, or stored therein or provided thereto, a number representing the number of pixels or a percentage of pixels which should be at or above the threshold value to provide the desired/optimal image. For example, in one case it may be known that a best image can be expected to be provided if 5% of the pixels are at or near saturation or above the threshold value. Alternately, rather than considering a percentage of pixels, the system may instead analyze the raw number of pixels that are at or near saturation or above the threshold value.

Thus, in the case of a 2.1 megapixel CCD array, and continuing to use the 5% number as an example, the system may use a number of 0.105 megapixels at the cut-off which are desired to be above the threshold value. Of course, the cut-off percentage and cut-off number of pixels can vary widely depending upon the type of image desired/expected, the properties of the equipment, etc. In addition, it should be understood that rather than utilizing the cut-off number at this point, projected values for each pixel can be generated, and then a threshold is applied, and/or the optimal exposure time calculated in other manners.

As mentioned above, in addition to using a percentage of pixels that can be at or above the threshold, a raw number of pixels can be used for this purpose. To determine the raw number of pixels that can be at or above the threshold, various methods can be utilized including but not limited to: A) analyzing the number of pixels typically encompassed by an object of interest on an image at different binning levels, resolutions, etc. and/or B) analyzing the number of pixels that reach saturation at different binning levels, resolutions, etc. using the maximum exposure time when no object is imaged (i.e., background such that only uncompensated random noise is present in the image).

It can be assumed that the intensity value for each pixel will increase linearly/proportionally, or at some known non-linear rate, with respect to increased exposure time. Thus once the data for the test image is known, and the threshold value for high intensity pixels are known, the optimal exposure time for the image can be calculated. Continuing with the example set forth above and assuming a linear relationship between pixel intensity and exposure time, it can be seen that if it is desired that the image have 0.105 megapixels of its 2.1 pixels be close to saturation (at or exceeding a threshold value of 58,982), the original exposure time (say, 15 seconds) should be multiplied by a number, which needs to be determined, to provide the desired output. For example, it may be determined that if the test exposure time is increased 4 times, 0.105 megapixels of the test image will be at and/or exceed the threshold value, resulting in an optimal exposure time of 4×15 seconds, or 60 seconds.

In one case, then, the optimal exposure time can be calculated by: 1) determining the number of pixels that are desired to exceed the threshold value; 2) from the test image data conducted at a test image exposure, selecting the number of pixels, from step 1, of pixels with the greatest intensity; 3) from the group of pixels defined in step 2) selecting the pixel with the smallest intensity value; 4) dividing the intensity value from step 3) by the time of the test image exposure; and 5) dividing threshold value by the numerical result of step 4), resulting in the optimal exposure time.

By way of example, consider the following 16 bit image data from a simple eight pixel array, which represents pixel output received after a 15 second exposure time:

TABLE 1

| Pixel Number | Pixel Output |
| --- | --- |
| 1 | 5,000 |
| 2 | 10,000 |
| 3 | 15,000 |
| 4 | 20,000 |
| 5 | 25,000 |
| 6 | 30,000 |
| 7 | 35,000 |
| 8 | 40,000 |

In this case, let it be assumed that it is desired that 25% of the pixels exceed a cut-off value of 58,982. In this case, then, under step 1 above it is determined that two pixels, or 25% of the eight total pixels, are desired to exceed the threshold value. Under step 2 from above, the two pixels of highest intensity are selected, which are pixels number 7 and 8. Under step 3, the pixel with the smallest intensity value between pixels 7 and 8 (pixel 7) is selected. The intensity value for pixel 7 (35,000) is then divided by the test time exposure (15 seconds) resulting in a value of 2333. The cut-off value (58,982) is then divided by 2333, resulting in a value of about 25.3 seconds. 25.3 seconds can then be considered the projected optimal exposure time.

Once the optimal projected exposure time is determined, a projected image can be generated, projecting/extrapolating how the image will look based upon the test image data, and assuming that intensity varies directly with exposure time (i.e. assuming a linear, or a known non-linear relationship between intensity and exposure time). Continuing with the example above, the pixel output of Table 1 will be multiplied by 25.3/15 resulting in the following output:

TABLE 2

| Pixel Number | Pixel Output |
|---|---|
| 1 | 8,433 |
| 2 | 16,867 |
| 3 | 25,300 |
| 4 | 33,733 |
| 5 | 42,167 |
| 6 | 50,600 |
| 7 | 59,033 |
| 8 | 65,535* (67,466) |

*In this example, values that exceed the maximum intensity for a pixel (65,535) are assigned the maximum intensity value (16 bit image)

In this case, then, it can be seen that 25% of the pixels exceed the pixel threshold of 58,982, as desired. Of course, there are a wide variety of mathematical methods and algorithms and pixel math techniques that can be utilized to determine an exposure time that is projected to provide a minimum number/percentage of pixels that exceed a threshold value, and the technique outlined above is simply one example. The system and method specified and claimed herein is not limited the specific technique shown above. In any case, once the projected optimal exposure time image is calculated, the projected image can be generated and presented to the user/operator.

Figure 2:
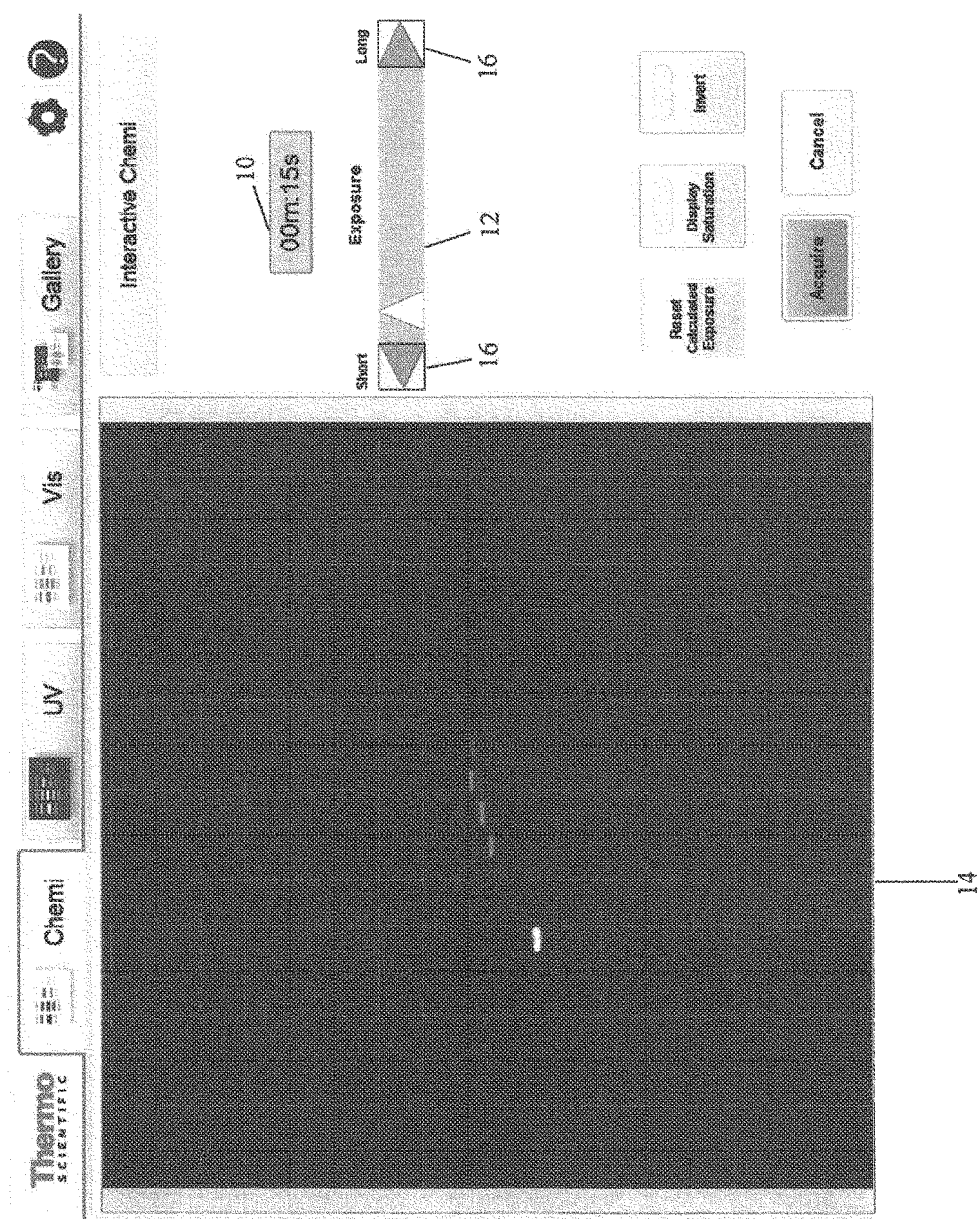
FIG. 2 is an image view of an object at an initial exposure time according to one embodiment of the invention.
Figure 3:
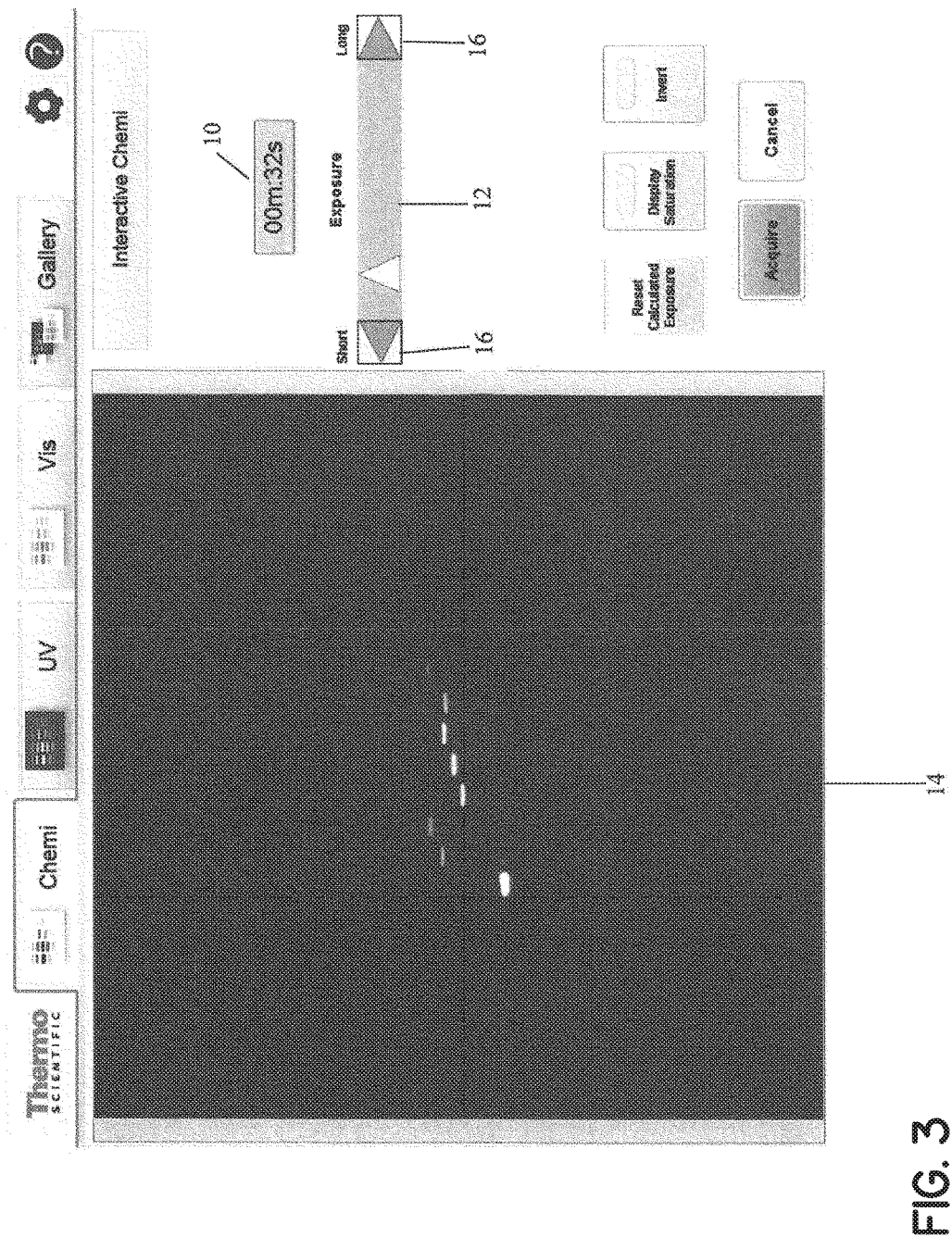
FIG. 3 is a projected image view of the object of FIG. 2 at an exposure time calculated to be optimal according to one embodiment of the invention.

For example, FIG. 2 illustrates a test image at a test exposure of ten seconds in the illustrated embodiment, as shown in the exposure time display 10. In this figure the image is slightly underexposed. The calculations outlined above can be applied to the image/image data of FIG. 2, resulting in a projected optimal exposure time of 17 seconds. FIG. 3, then, shows an image based upon the data/image of FIG. 2 as presented to a user at a projected optimal exposure time, or a second exposure time. In this case the projected optimal exposure time is 17 seconds, as calculated by the system in the manner outlined above.

The system may also provide the option to a user to manually adjust the exposure time (i.e. via a user input device, resulting in a third or user-created exposure time), and the system can adjust the projected image accordingly. In other words, each pixel output can be adjusted in a manner directly proportional to the input exposure time to present an image to the user/operator, so that the user/operator can see how the image is projected to look at a user-defined exposure time. In the illustrated embodiment, the input device takes the form of slider bar 12 that can be adjusted by a user via a cursor control device of the like. In one case, the projected image 14 is displayed in real time to match the position of the slider bar 12 as it is moved so that the user/operator is provided with instantaneous feedback.

When the slider bar 12 is utilized, the numerical value of the exposure time is displayed in the exposure time display 10. Alternately, or in addition, the user/operator may be able to directly enter the numerical value of the desired exposure time to be displayed, or control the numerical values with navigation buttons 16, etc.

Figure 4:
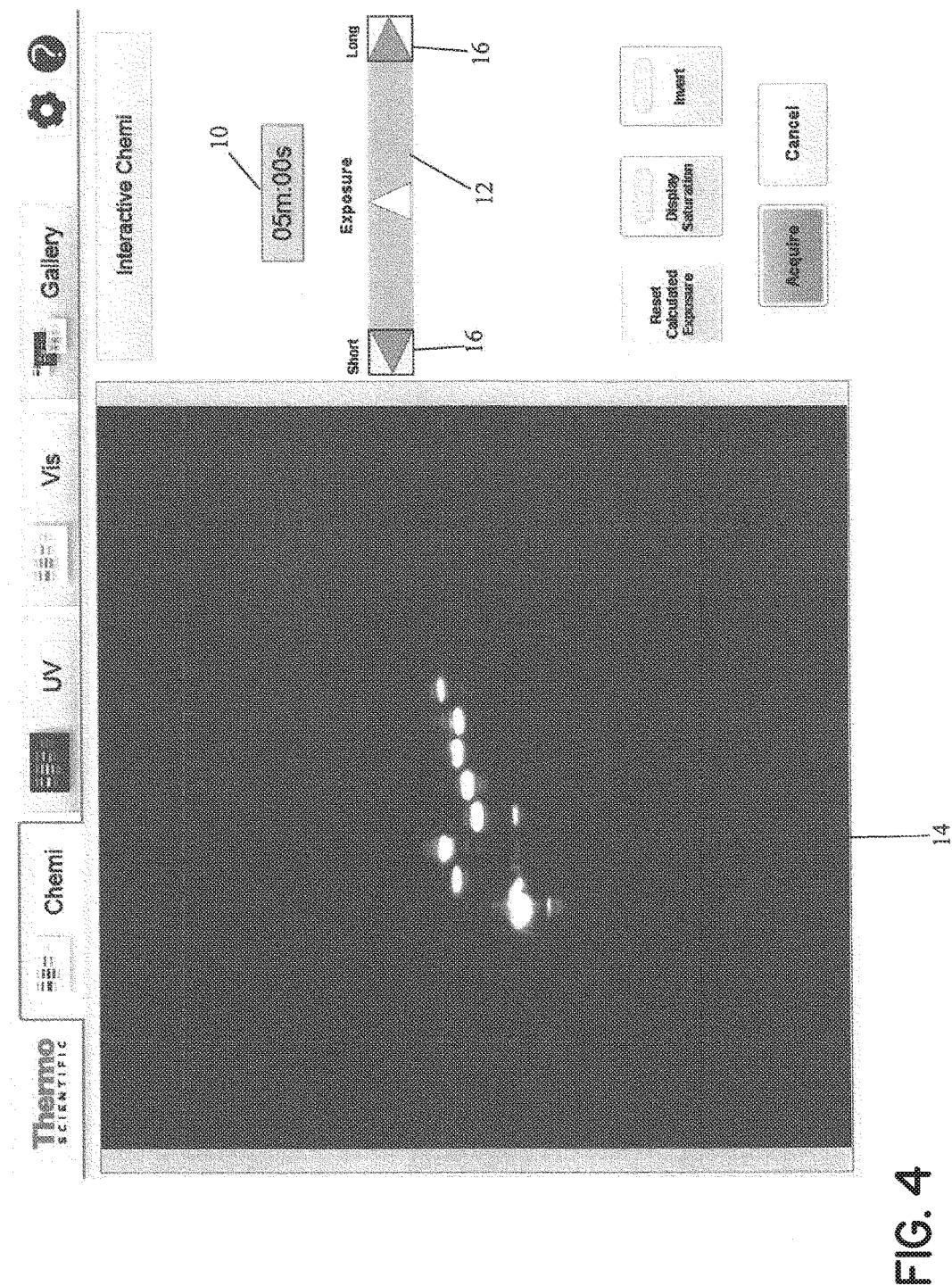
FIG. 4 is a projected image view of the object of FIG. 2 at an exposure time longer in duration than that of FIG. 3 according to one embodiment of the invention.
Figure 5:
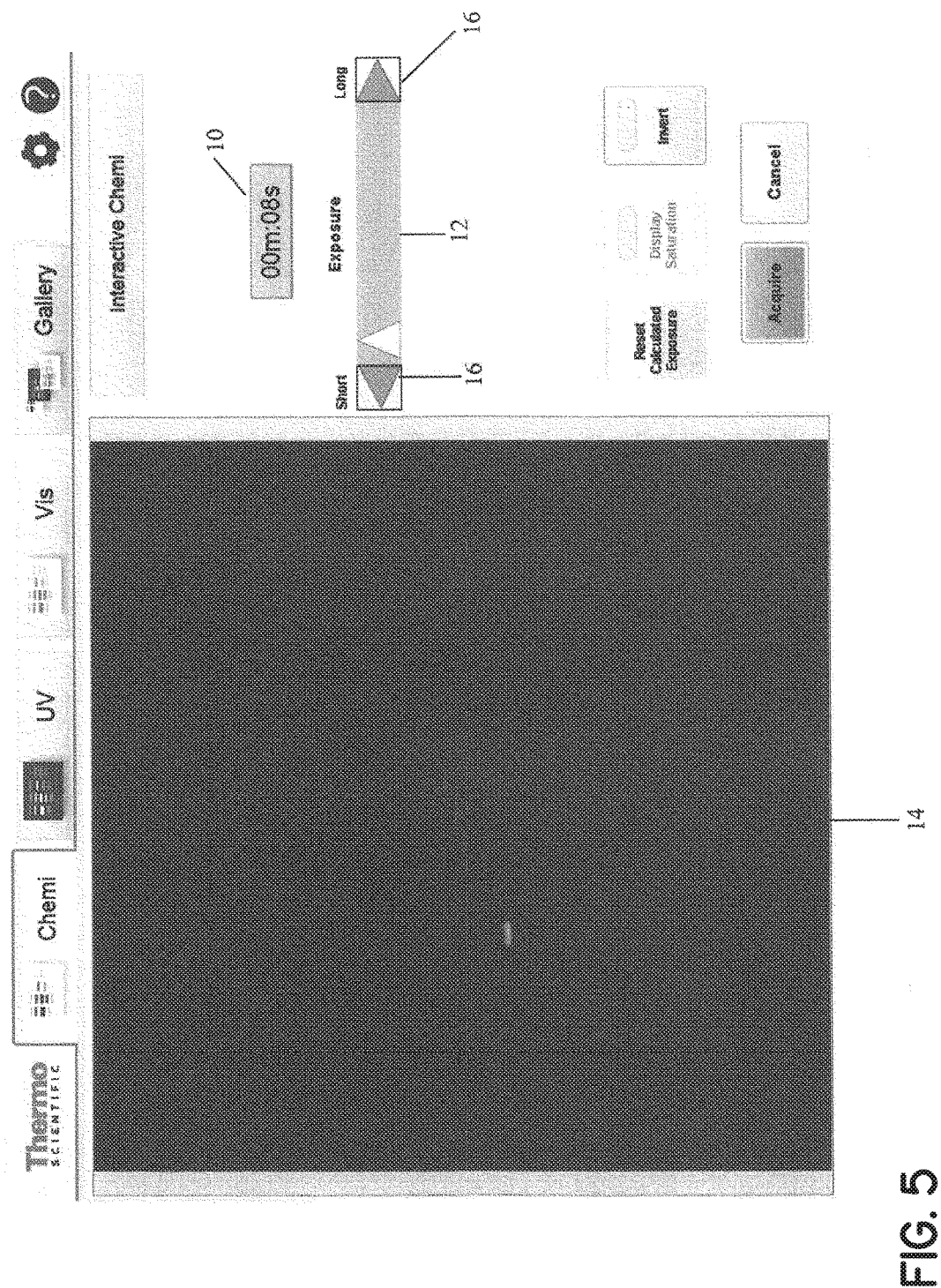
FIG. 5 is a projected image view of the object of FIG. 2 at an exposure time shorter than that of FIG. 3 according to one embodiment of the invention.

Thus, while the system can generate a projected optimal exposure time, it is understood that in some cases the user/operator may desire an exposure time different from the calculated optimal exposure time, based upon the user/operator's review of the displayed projected image. FIG. 4 presents a projected image 14 where the user/operator had increased the exposure time (to 5 minutes, in the illustrated embodiment) to the point where the image 14 is over-exposed. FIG. 5 presents a projected image where the user/operator had decreased the exposure time (to 8 seconds, in the illustrated embodiment) to the point where the image 14 is under-exposed.

Figure 6:
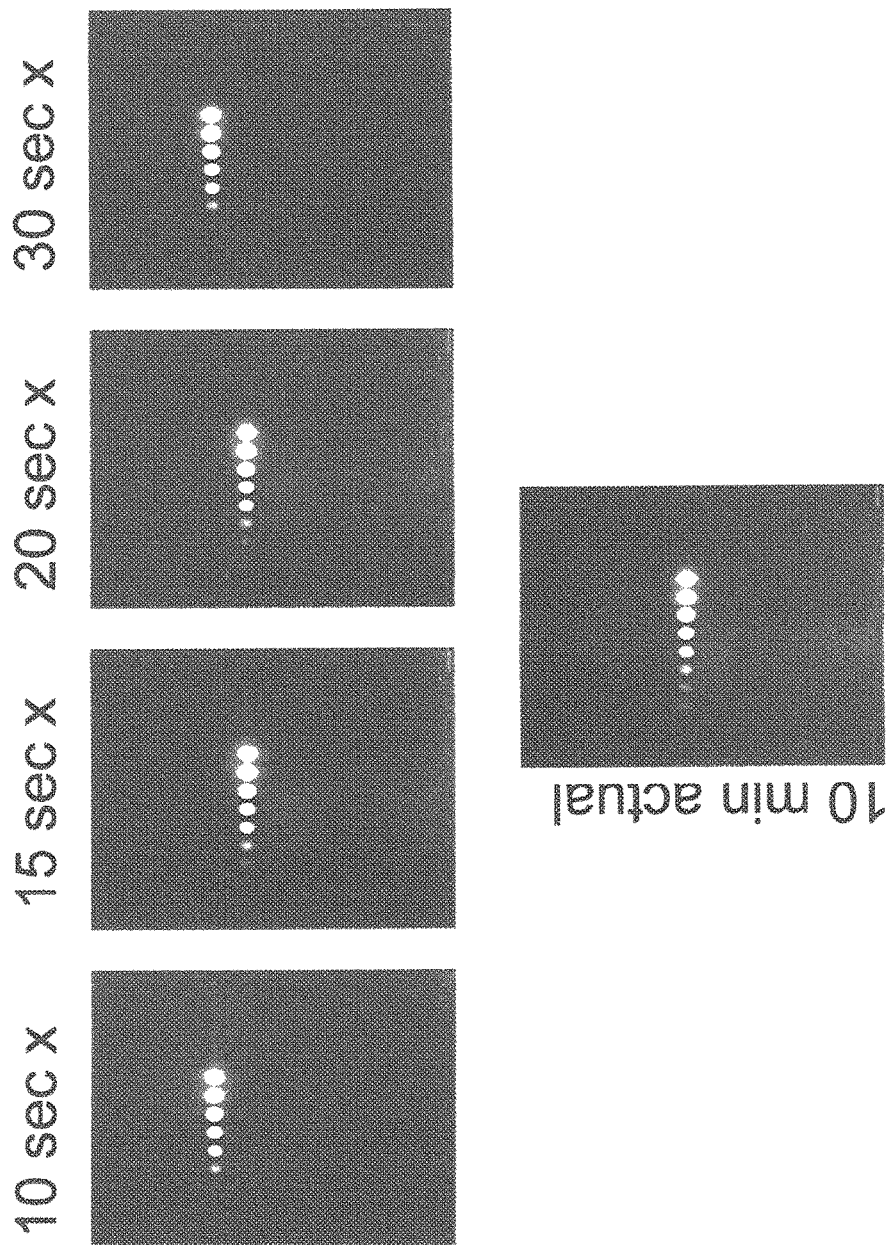
FIG. 6 depicts various projected image views, at a 10 minute exposure time, as compared to an actual image at a 10 minute exposure time according to one embodiment of the invention.

The test/initial exposure time can be selected to provide an accurate baseline image for use in projecting images and/or determining optimal exposure times, while also providing convenience for the user. In particular, the longer the test/initial exposure time, the more accurate the (longer exposure time) projected image(s) will be. FIG. 6 illustrates estimated images for a ten minute exposure image, based upon test/initial exposure times of 10 seconds, 15 seconds, 20 seconds, and 30 seconds. FIG. 6 also illustrates an actual image taken at 10 minutes. As can be seen, the longer the initial exposure time (or closer to the actual exposure time), the more accurate the projected image. On the other hand, making the initial exposure time too long can take up time and resources.

The user can modify the exposure time and/or accept the projected optimal exposure time as presented by the system, to select/define the optimal/desired exposure time. Once the optimal/desired exposure time is selected/defined, an image can be acquired at the selected/defined exposure time and used for further processing. The actual image acquired at the optimal or selected exposure time will, of course, vary from the projected/preview images as outlined above. In particular, in the projected/preview images based upon the test image, the noise levels will be disproportionally increased as compared to the actual image acquired at the optimal/selected exposure time. Therefore, further noise reduction processes can be applied to create clean projected/preview images. However the system and method enables optimal exposure time to be determined/selected using, in one case, only a short, preliminary image acquisition time. The test image may not, in some cases, provide visual data to a human viewing the image, but may provide sufficient information after analysis to provide the benefits outlined above. The system and method can be used with nearly any light imaging system, but may find particular utility with detecting low light objects.

In one case, the creation and display of projected images at differing exposure times, and/or the determination of optimal exposure time, can be limited to only a certain area or portion of the test/initial image. In particular, in some cases the test/initial image may include the entire substrate or object, along with a background area. The object and background area may be present a relatively high contrast when imaged. For example, the object may be generally white or light, and the background may be generally black or dark. In this case, or in other cases where possible, it may be advantageous to distinguish the object from the background area, and apply the techniques described herein only to the object/substrate.

Figure 7:
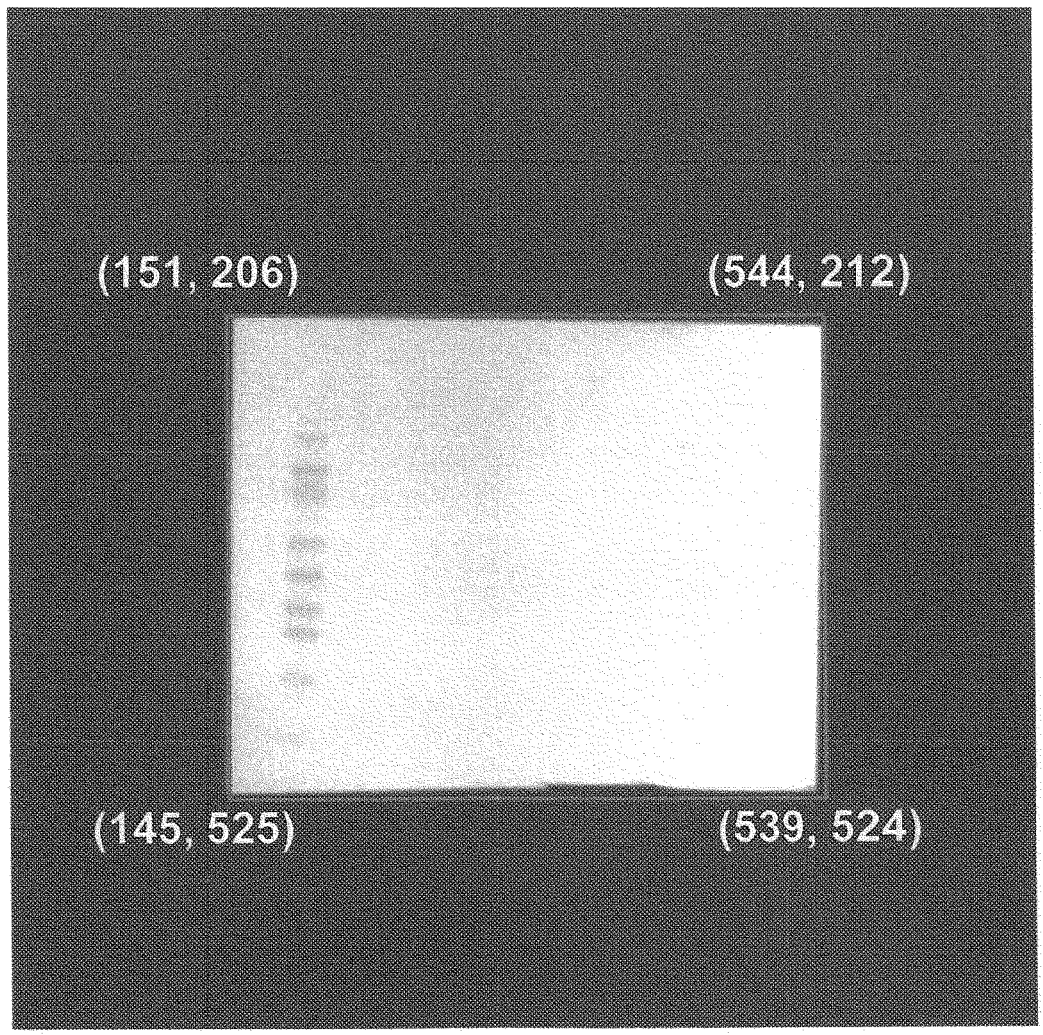
FIG. 7 is an image view of an object in front of a background according to one embodiment of the invention.

For example, FIG. 7 shows an image of a light substrate/object in front of a dark background. After this test/initial image is acquired, the system/method may determine the outline of the object. Due to the high contrast between the object and the background of FIG. 7, any of a wide variety of edge-locating or contrast-locating algorithms may be utilized to determine the boundary between the object and background. In the illustrated embodiment the corners of the object are located using well-known corner-locating algorithms, and the edges of the object determined by projecting straight lines between the corners. Of course, the object can have various other shapes besides rectangular, in which case other suitable algorithms are utilized to determine the outer edges of the object.

Once the shape and dimensions of the object are determined, all data relating to areas outside the object can be ignored, and not form the basis for any further image projecting or optimal exposure time determinations as outlined above. For example, in one case each pixel determined to be outside the object is set to an arbitrary value (0, in one example), or each pixel simply remains at its value from the initial/test image. In either case, the exposure processing outlined above is carried out only on the image pixels determined to be on/within the object, which can significantly reduce amount of pixels to be processed. This process thereby enables more rapid calculations, providing a quicker response time and saving computing resources.

Thus, as outlined above, only a portion of the originally-acquired image, or a region of interest ("ROI"), may be utilized for the creation and display of projected images at differing exposure times, and/or the determination of optimal exposure time. In the illustrated embodiment, the entire substrate/object forms the ROI. However, the ROI can constitute various other areas, such as particular areas of interest in the substrate/object.

As noted above, a threshold value may be determined for a particular image captured at a particular exposure time. The threshold value is the intensity value that an individual pixel included in the particular image is to reach and/or exceed in order to satisfy the threshold value. The image may sufficiently display the particular characteristics necessary for a user to adequately analyze the specimen when a sufficient percentage of pixels included in the particular image that each satisfy the threshold value is reached. The intensity value for a pixel is the amount of energy that the pixel emits relative to the detection capabilities of the detector that the pixel is associated with. An increased intensity value for a pixel may trigger an increased sensitivity of the detector that the pixel is associated with such that the pixel contributes to a higher quality image. The greater the intensity value generated by the greater percentage of pixels may result in an increased sensitivity of the detector associated with each of the pixels and thus generating a higher quality image.

The intensity value for each pixel may range from zero to a saturation value that is based on the total quantity of pixels included in an image. For example, each pixel included in a 16 bit image may have an intensity value that ranges from 0 to 65,535. The intensity value of each pixel may be based on various factors including the exposure time in which each pixel is exposed to capturing the image. The exposure time is the amount of time that each pixel is exposed to the energy emitted by an environment that the imaging system is attempting to capture. As the exposure time for each pixel increases, the amount of energy that is detected by each pixel increases based on an increase in sensitivity of the detector that each pixel is associated with thus resulting in an increased intensity value for each pixel. As the exposure time for each pixel increases, the intensity value for each of the pixels may also increase resulting in a higher quality image.

The threshold value may be a percentage that represents an intensity value as compared to the saturation value that a pixel included in the image is to satisfy. The saturation value may be the maximum intensity value that the pixel may reach. The greater percentage of pixels that satisfy the threshold value results in a greater percentage of pixels that have intensity values that are within a percentage of the saturation value that results in a higher quality image. The percentage of pixels that have intensity values that are within a percentage of the saturation value to generate an image of sufficient quality such that the user may adequately analyze the specimen is the pixel intensity saturation level threshold.

For example, the pixel intensity saturation level threshold that is to be satisfied to generate a 16 bit image of sufficient quality is to have 10% of the total pixels in an image that have intensity levels that exceed 64,000. In other words, the intensity saturation level threshold that is to be satisfied for the 16 bit image which is to have 10% of the total pixels in an image satisfy a threshold value of 97% in which an intensity level of 64,000 is 97% of the saturation value of 65,535 for a 16 bit image.

In an embodiment, the pixels included in the image that have intensity values with the highest intensity as compared to the remaining pixels included in the image that have lower intensity values may be selected to generate an image of sufficient quality such that the user may adequately analyze the specimen. The pixels may be evaluated to determine whether each pixel included in the image is included in the intensity threshold percentage. The intensity threshold percentage may be a percentile of pixels that have the highest intensity levels as compared to the remaining pixels not included in the intensity threshold percentage. For example, the intensity threshold percentage may include pixels included in the image that have intensity levels that are in the top 1% as compared to the intensity levels of the pixels in the remaining 99%. The intensity threshold percentage may be adjusted by the user.

As noted above, the intensity value of each pixel may be increased as the exposure time for each pixel increases. However, a maximum exposure time may exist in which each pixel may become oversaturated if exposed to the energy emitted by the environment beyond the maximum exposure time. The detector that each pixel is associated with may no longer exercise its detection characteristics if exposed to a significant amount of energy emitted by the environment after being exposed to such energy for the maximum exposure time. Pixels that are oversaturated may negatively impact the quality of the image.

Thus, the threshold value for a particular image that the pixels are to satisfy in order to satisfy the pixel intensity saturation level threshold of the particular image may be determined. For example, the threshold value of a 16 bit image that the pixels are to satisfy in order to satisfy the pixel intensity saturation level threshold is 90% where the pixels to satisfy the threshold value are to have an intensity value of 58,981 which is 90% of the saturation value of 65,535 for a 16 bit image. The percentage of pixels that then satisfy the threshold value of 90% to satisfy the pixel intensity saturation level threshold is 15% where 15% of the total pixels in the 16 bit image satisfy the threshold value of 90% where 15% of the total pixels have intensity values that reach and/or exceed 58,981.

After the threshold value to be utilized is determined or otherwise set for the particular image, the exposure time that is required to ensure that the portion of pixels satisfy the threshold value may be determined. However, determining the exposure time that is required to ensure the pixel intensity saturation level threshold of particular image is satisfied may not be an optimal exposure time in order to attain an increased percentage of pixels that satisfy the threshold value. As noted above, the threshold value is the percentage of the saturation value for the particular image that an individual pixel is to satisfy in order to satisfy the threshold value.

However, the quality of the image that is to be evaluated by the user not only increases based on the threshold value for an individual pixel in the particular image to satisfy but also the percentage of pixels included in the particular image that satisfy the threshold value which is the pixel intensity saturation level threshold. As noted in the example above, 15% of the pixels included in the particular image are required to satisfy the threshold level of having intensity levels within 90% of the saturation level of the particular image in order to generate an image of sufficient quality for the user to adequately examine the specimen.

The percentage of pixels that have intensity values that satisfy the threshold value may also increase as the exposure time increases. For example, a first image may have 40,000 pixels that satisfy the threshold level of 90% with an exposure time of 10 ms while a second image may have 45,000 pixels that satisfy the threshold level of 90% with an exposure time of 20 ms. Despite both the first image and the second image satisfying the threshold level of 90%, the second image with an exposure time of 20 ms has a greater percentage of pixels that exceed the threshold level of 90% as compared to the first image with an exposure time of 10 ms that also exceeds the threshold level of 90%. Thus, simply determining the exposure time such that individual pixels included in a particular image satisfy the threshold level based on a particular exposure time may not result in an optimal exposure time with an increased percentage of pixels that satisfy the threshold level.

As a result, simply determining an exposure time such that individual pixels included in a particular image satisfy the threshold level based on a particular exposure time may limit the percentage of pixels that satisfy the threshold level. As noted in the example above, simply determining an exposure time of 10 ms because the exposure time is a relatively short exposure time allowing a significant increase in specimens that may be analyzed in a given period of time may result in a significantly less percentage of pixels that satisfy the threshold level as compared to an exposure time of longer duration.

However, simply determining an exposure time that has a significant increase in duration to ensure that the maximum percentage of pixels that satisfy the threshold level is attained increases the risk in oversaturation of the pixels. As noted above, oversaturation of the pixels may occur when the pixels are exposed to the energy emitted by the environment to an extent that the detection characteristics of the detector that the pixels are associated with are no longer exercised resulting in a negative impact on the image by the oversaturated pixels. Further, a significantly increased exposure time may also unnecessarily increase the amount of time required to analyze each specimen and thus decreasing the amount of specimens that may be analyzed during a period of time when an exposure time of shorter duration may adequately provide an image with sufficient quality for the user to adequately examine the specimen while increasing the amount of specimens that may be analyzed during the period of time.

Rather than determining the optimal exposure time from a single image, the optimal exposure time may be determined from a linear relationship that exists between multiple images each captured at different exposure times. As noted above, the percentage of pixels that have intensity values that satisfy the threshold value may increase as the exposure time increases. Thus, for each individual image captured at a different exposure time has a corresponding percentage of pixels that satisfy the threshold value that increases for each increased exposure time. The linear relationship between the percentages of pixels that satisfy the threshold value for the multiple images may be determined to project the optimal exposure time in order to capture an increased percentage of pixels that exceed the pixel intensity saturation level threshold without oversaturation.

Figure 8:
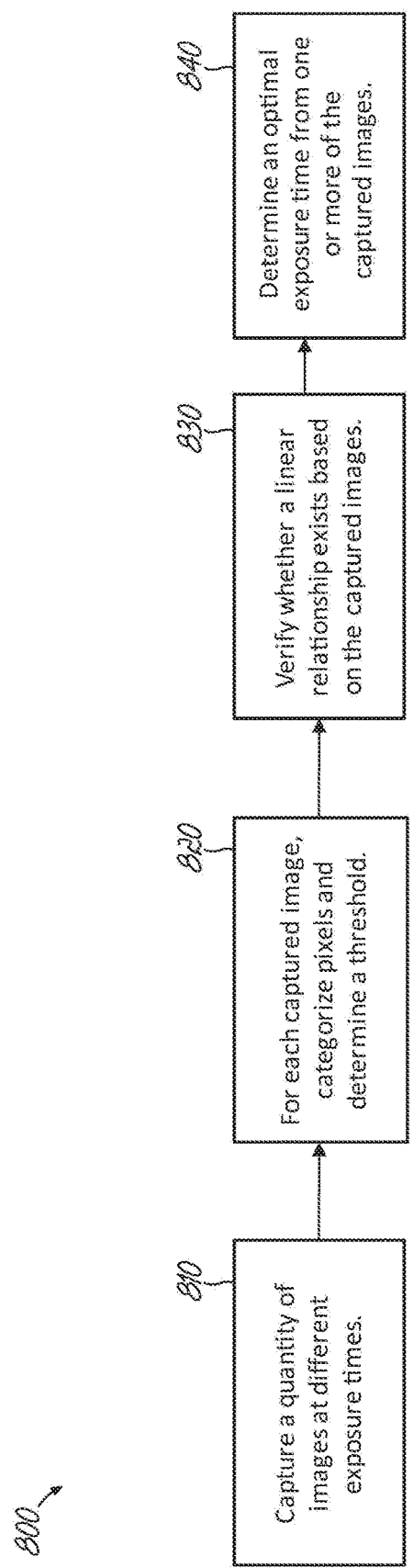
FIG. 8 is a flowchart of an exemplary process for determining the optimal exposure time for an image according to one embodiment of the invention.

One such implementation of determining the optimal exposure time for an image is illustrated by process 800 in FIG. 8. Process 800 includes four primary steps: capture a quantity of images at different exposure times 810, for each captured image, categorize pixels and determine a threshold 820, verify whether a linear relationship exists based on the captured images 830, and determine an optimal exposure time based on at least one of the captured images 840. Steps 810-840 are typically implemented in a computer, e.g., via software and/or hardware, e.g., computer system 100 of FIG. 13.

Figure 9:
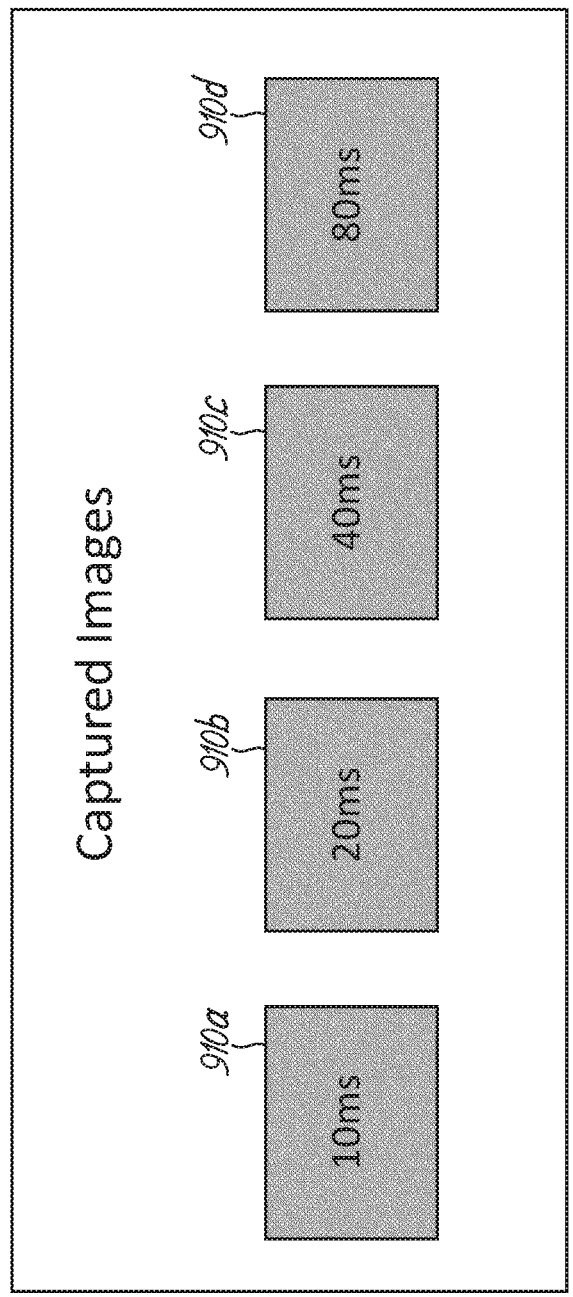
FIG. 9 is an image view of images captured at different exposure times according to one embodiment of the invention.

In step 810, a quantity of images may be captured at different exposure times. As shown in FIG. 9, a plurality of images 910(*a-n*), where n is an integer equal to or greater than three, may be captured with each of the images 910(*a-n*) being captured at different exposure times. Each of the exposure times for each of the corresponding images 910 (*a-n*) may be determined such that a range of exposure times in which different percentages of the pixels that satisfy the threshold value may be generated.

The exposure times may range from a first exposure time that has a shortest exposure time duration for the corresponding image 910*a* to an nth exposure time that has a longest exposure time duration for the corresponding image 910*n*. The first exposure time with the shortest exposure time duration may be sufficient in duration such that a percentage of the pixels included in the corresponding image 910*a* satisfy the threshold. The nth exposure time with the longest exposure time duration may be greater than each of the exposure times for corresponding images 910(*a-c*) without having oversaturated pixels.

Figure 13:
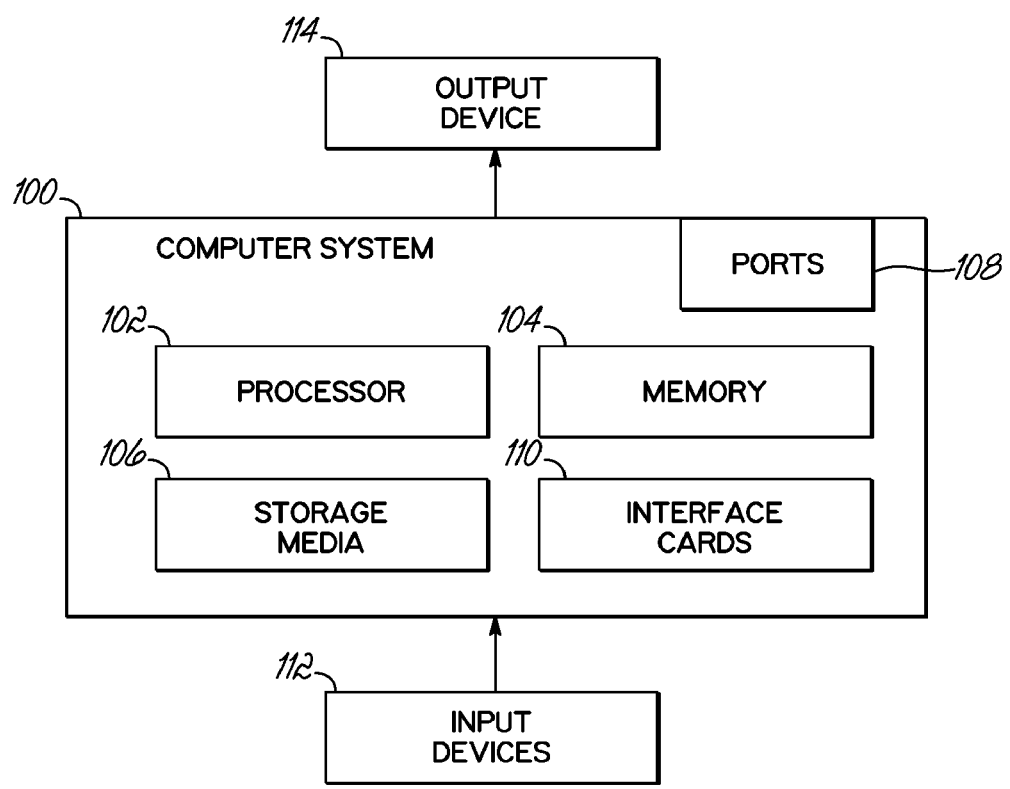
FIG. 13 is a schematic view of a general purpose computer system suitable for operating the method and system disclosed herein according to one embodiment of the invention.

The quantity of images 910(*a-n*) may include a minimum of three images such that a linear relationship may be established between three exposure times that correspond to the minimum of three images. However, the quantity of images 910(*a-n*) may range up to any quantity of images greater than three. As the quantity of images 910(*a-n*) increases, the accuracy of the resulting linear relationship between the different exposure times that correspond to each of the images 910(*a-n*). For example, the exposure time for image 910*a* may be 10 ms, the exposure time for image 910*b* may be 20 ms, the exposure time for image 910*c* may be 40 ms, and the exposure time for image 910*n* may be 80 ms. In an example embodiment, step 810 may be performed by processor 102 of computer system 100 as shown in FIG. 13.

The different exposure times for images 910(a-n) may be based upon preset defaults tailored to a particular application, e.g., fluorescent or chemiluminescent detection, and may also be customized by a user.

Figure 10:
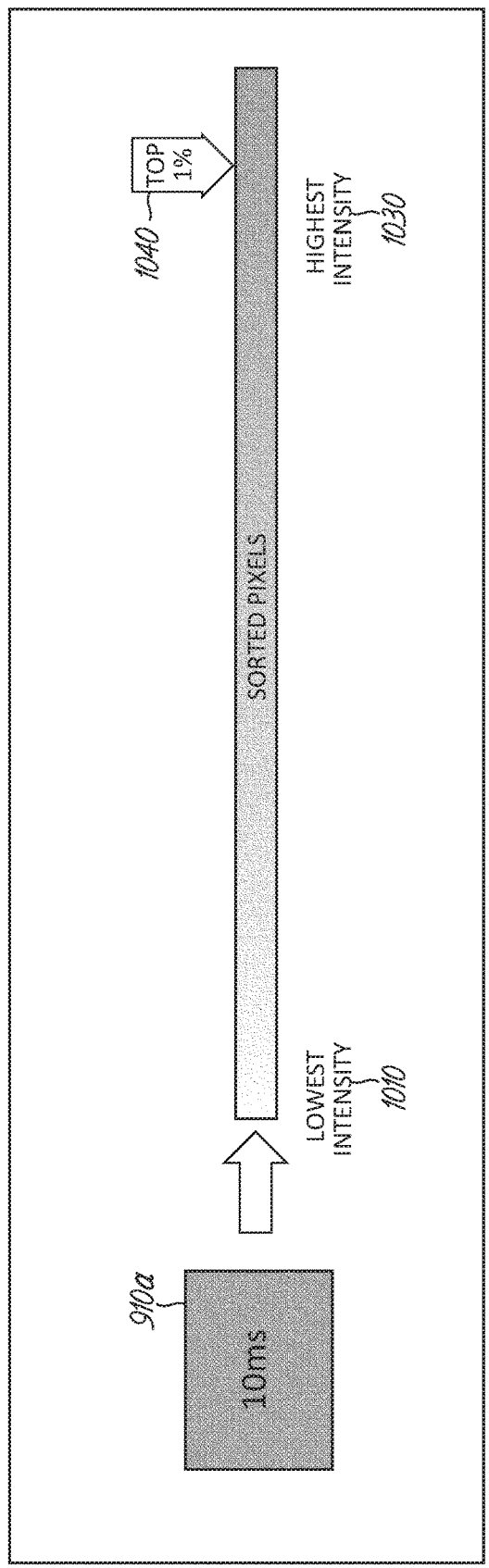
FIG. 10 is an image view of a threshold value that is determined for the images and each of the pixels included in each of the images is sorted based on the threshold value according to one embodiment of the invention.

In step 820, the pixels for each of the images 910(a-n) may be categorized based on whether the pixels satisfy an intensity threshold percentage. As shown in FIG. 10, an intensity threshold percentage for the images 910(a-n) may be determined and each of the pixels included in each of the images 910(a-n) may be sorted based on the intensity threshold percentage. The intensity threshold percentage may be a percentile of pixels that have the highest intensity levels as compared to the remaining pixels not included in the intensity threshold percentage. For example, the intensity threshold percentage may include pixels included in the image that have intensity levels that are in the top 1% as compared to the intensity levels of the pixels in the remaining 99%. The intensity threshold percentage may be based upon preset defaults tailored to a particular application, and may also be adjusted by the user.

As noted above, the threshold value for each of the images 910(a-n) may be determined such that the intensity value for an individual pixel is to be within a percentage of the saturation value for the image in order for the individual pixel to satisfy the threshold. The intensity value that each individual pixel may have may range from the lowest intensity 1010 when the individual pixel has the lowest intensity value such as approximately zero to the highest intensity 1030 when the individual pixel has a highest intensity value when the individual pixel is saturated.

The intensity threshold percentage 1040 for each of the images 910(a-n) may be determined such that the same intensity threshold percentage 1040 is applied to each of the images 910(a-n). As noted above, the quality of the image not only increases based on whether an individual pixel is included in the intensity threshold percentage 1040 but also the percentage of the pixels that are included in intensity threshold percentage 1040. In order for the linear relationship between the percentage of pixels that are included in the intensity threshold percentage 1040 for each of the images 910(a-n) to be determined, the intensity threshold percentage 1040 applied to each of the images 910(a-n) is constant. For example, the intensity threshold percentage 1040 applied to each of the images 910(a-n) is 99% such the pixels with intensity levels in the top 99% of the pixels included in the image are included in the intensity threshold percentage 1040.

After each of the pixels that have intensity levels that are included in the intensity threshold percentage 1040, such as the pixels with intensity levels that are in the 99$^{th}$ percentile as compared to the remaining pixels included in the image, are selected, those selected pixels may then be evaluated. A lower intensity threshold and an upper intensity threshold may be established for the selected pixels that are included in the intensity threshold percentage 1040. The lower intensity threshold may be a lower intensity value that may exclude pixels included in the intensity threshold percentage 1040 with intensity values that are below the lower intensity threshold. The upper intensity threshold may be an upper intensity value that may exclude pixels included in the intensity threshold percentage 1040 with intensity values that are above the upper intensity threshold.

The lower intensity threshold may be a lower intensity value threshold that filters out pixels included in the intensity threshold percentage 1040 with intensity values that may be associated with noise. The lower intensity threshold may be an intensity value that an intensity value of a pixel is to exceed in order to ensure that the intensity value of the pixel is not associated with noise. For example for a 16 bit image with an intensity threshold percentage 1040 of 99%, the lower intensity threshold may be 64,979 which is a value that is 100 units higher than the intensity value of 64,879 which is the intensity value that is within 99% of the saturation value of a 16 bit image of 65,535. Any pixel included in the intensity threshold percentage 1040 that exceeds the lower intensity threshold of 64,979 may be considered as a pixel reflects the actual signal rather than noise. The user may adjust the lower pixel intensity threshold, which may also be preset based upon a particular application and/or the characteristics of the system responsible for imaging the specimen (e.g., the specific properties of the excitation source(s) or the detector).

The upper intensity threshold may be an intensity value threshold that filters out pixels included in the intensity threshold percentage 1040 with intensity values that may be oversaturated. The upper intensity threshold may be an intensity value that an intensity value of a pixel is to fall below in order to ensure that the intensity value of the pixel is not oversaturated. For example, a 16 bit image with an intensity threshold percentage 1040 of 99%, the upper intensity threshold may be 65,435 which is a value that is 100 units lower than the saturation value of 65,535 for a 16 bit image. Any pixel included in the intensity threshold percentage 1040 that falls below the upper intensity threshold of 65,435 may be considered as a pixel that is not oversaturated. The user may adjust the upper intensity threshold, which may also be preset based upon a particular application and/or the characteristics of the system responsible for imaging the specimen (e.g., the specific properties of the excitation source(s) or the detector).

Each of the pixels that have intensity levels that are above the lower intensity threshold and below the upper intensity threshold may then be included in the linear relationship determination discussed below in detail in step 820. In an example embodiment, step 820 may be performed by processor 102 of computer system 100 as shown in FIG. 13.

Figure 11:
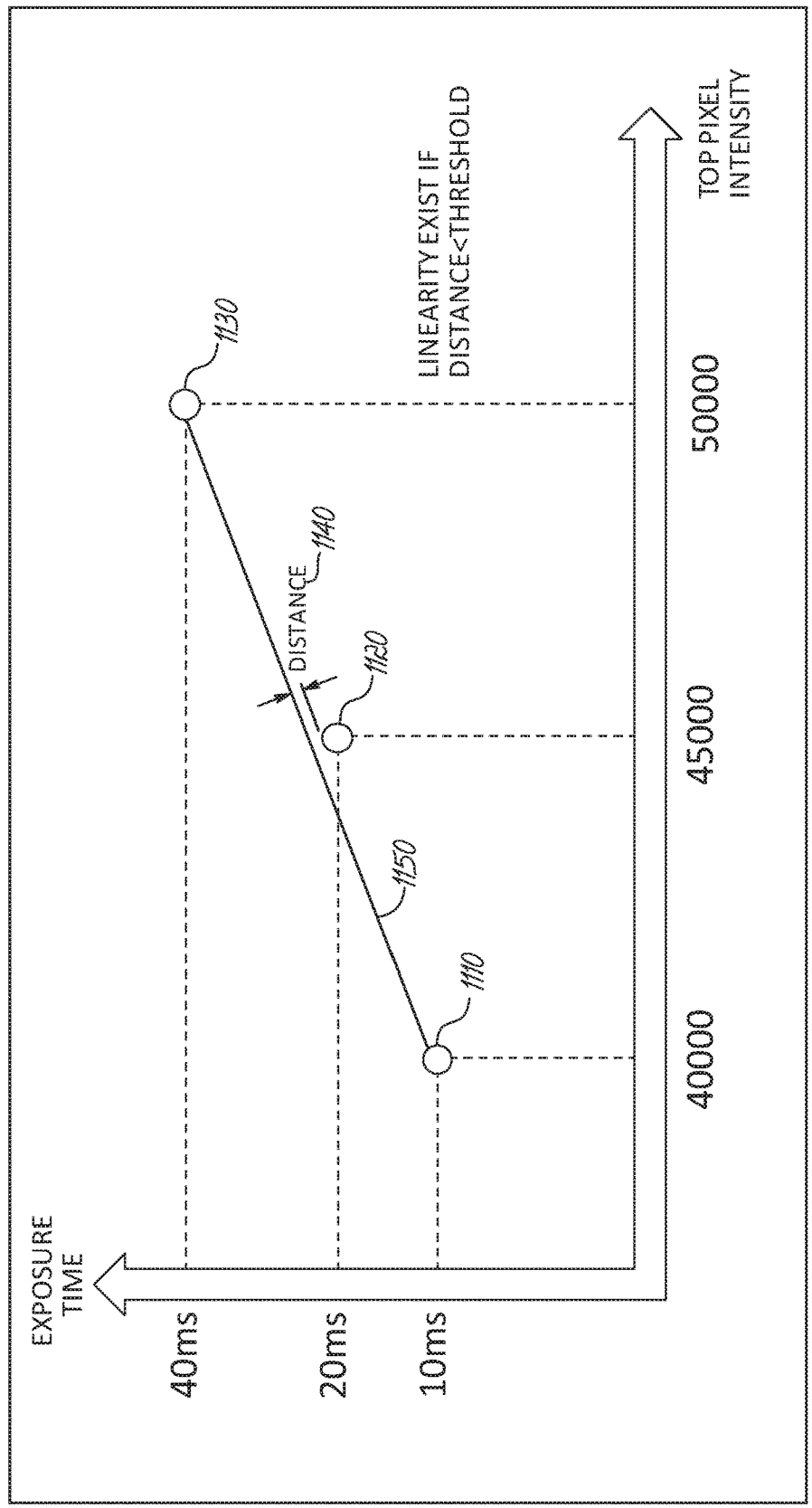
FIG. 11 is an image view of relationships that are plotted for each of the images according to one embodiment of the invention.

In step 830, whether a linear relationship exists based on the captured images is verified. As shown in FIG. 11, relationships 1110, 1120, and 1130 are plotted for each of the images 910(a-n). For example, relationship 1110 represents the relationship between the exposure time of 10 ms and the percentage of pixels of 40,000 that satisfy the lower intensity threshold and the upper intensity threshold for image 910. Relationship 1120 represents the relationship between the exposure time of 20 ms and the percentage of pixels of 45,000 that satisfy the lower intensity threshold and the upper intensity threshold for image 910b. Relationship 1130 represents the relationship between the exposure time of 40 ms and the percentage of pixels 50,000 that satisfy the lower intensity threshold and the upper intensity threshold of image 910n. As noted above, the intensity threshold percentage applied to each of the images 910(a-n) is constant and the different exposure times increase from a shortest exposure time duration in 10 ms to a longest exposure time duration in 40 ms.

In order to determine whether a linear relationship exists between each of the relationships 1110, 1120, and 1130, a theoretical linear relationship 1150 between relationship 1110 and 1130 may first be determined. The theoretical linear relationship 1150 is the linear relationship that would exist between the image 910a with the exposure time with a first duration, as represented by relationship 1110 in this example, and the image 910n with the exposure time with a second duration, as represented by relationship 1130 in this example. The exposure time with a first duration is shorter than the exposure time with a second duration.

However, as noted above, in order to determine the optimal exposure time to obtain the percentage of pixels that satisfy the threshold to generate an image enables the user to adequately analyze the specimen, any amount of images with different exposure times as well as a single image with a single exposure time may be incorporated. However, for ease of discussion, the following example discusses incorporating three images with three different exposure times.

After the theoretical linear relationship 1150 is determined between the relationship 1110 with the first exposure time duration and the relationship 1130 with the second exposure time duration, the relationship 1120 with the exposure time duration that is between the exposure time durations of relationship 1110 and relationship 1130 may be compared to the theoretical linear relationship 1150. The distance 1140 of the relationship 1120 from the theoretical linear relationship 1150 may be compared to a threshold distance to determine whether a linear relationship exists between relationships 1110, 1120, and 1130.

The threshold distance is a distance from the theoretical linear relationship 1150 that when relationship 1120 is within the threshold distance, a linear relationship exists between relationships 1110, 1120, and 1130 such than an adequate optimal exposure time may be determined from the linear relationship to obtain the appropriate percentage of pixels that satisfy the threshold to generate an image that enables the user to adequately analyze the specimen. For example, image 910*b* with an exposure time duration of 20 ms as represented by relationship 1120 is between the image 910*a* with the first exposure time duration of 10 ms as represented by relationship 1110 and the image 910*n* with the second exposure time duration of 40 ms as represented by relationship 1130. The theoretical linear relationship 1150 between relationship 1110 and 1130 is then determined.

The distance 1140 of relationship 1120 is then compared to the threshold distance to determine whether the distance 1140 is within the threshold distance. An adequate linear relationship between the relationships 1110, 1120, and 1130 to determine an adequate optimal exposure time to obtain the appropriate percentage of pixels that satisfy the pixel intensity saturation level threshold to generate an image that enables the user to adequately analyze the specimen when the distance 1140 of relationship 1120 is within the threshold distance. Thus, the optimal exposure time may then be calculated when the distance 1140 of the relationship 1120 is within the threshold distance based on the adequate linear relationship between the relationships 1110, 1120, and 1130.

However, an inadequate linear relationship between the relationships 1110, 1120, and 1130 exists when the distance 1140 of relationship 1120 is beyond the threshold distance. The distance 1140 of relationship 1120 being beyond the threshold distance is indicative that a weak linear relationship exists between the relationships 1110, 1120, and 1130. Attempting to determine the optimal exposure time based on a weak linear relationship may actually result in an exposure time that is less than optimal which would result in capturing a lesser percentage of pixels that satisfy the threshold in the image and thus resulting in a lesser quality image that hinders the user's ability to adequately analyze the specimen.

Rather than moving forward with determining an exposure time that is likely less than optimal when the distance 1140 of relationship 1120 is beyond the threshold distance, an additional image may be captured with an exposure time that has an exposure time duration that exceeds the second exposure time duration of relationship 1130. An adjusted theoretical linear relationship may then be determined based on image 910*a* represented by relationship 1110, image 910*b* represented by relationship 1120, and image 910*n* represented by relationship 1130 as well as the additional image with an exposure time duration that exceeds the longest exposure time duration of relationship 1130.

In this example, an additional image is captured with an exposure time duration that exceeds the first exposure time duration of 40 ms of relationship 1130. The distance 1140 for relationship 1120 may then be recalculated and compared to the threshold distance relative to the adjusted theoretical linear relationship as opposed to the initial theoretical linear relationship to determine whether an adequate linear relationship exists between relationships 1110, 1120, 1130, and the additional image. If so, the optimal exposure time may then be calculated based on the additional image. If not, yet another image may be captured with another exposure time that exceeds each of the previous exposure time durations to determine whether the distance 1140 for relationship 1120 is within the threshold distance. This is then repeated until the distance for relationship 1120 is within the threshold distance. In an embodiment, the first exposure time duration of relationship 1110 may be a shortest exposure time duration for the relationships 1110, 1120, and 1130 and the second exposure time duration of relationship 1130 may be a longest exposure time duration for the relationships 1110, 1120, and 1130. In an example embodiment, step 830 may be performed by processor 102 of computer system 100 as shown in FIG. 13.

Figure 12:
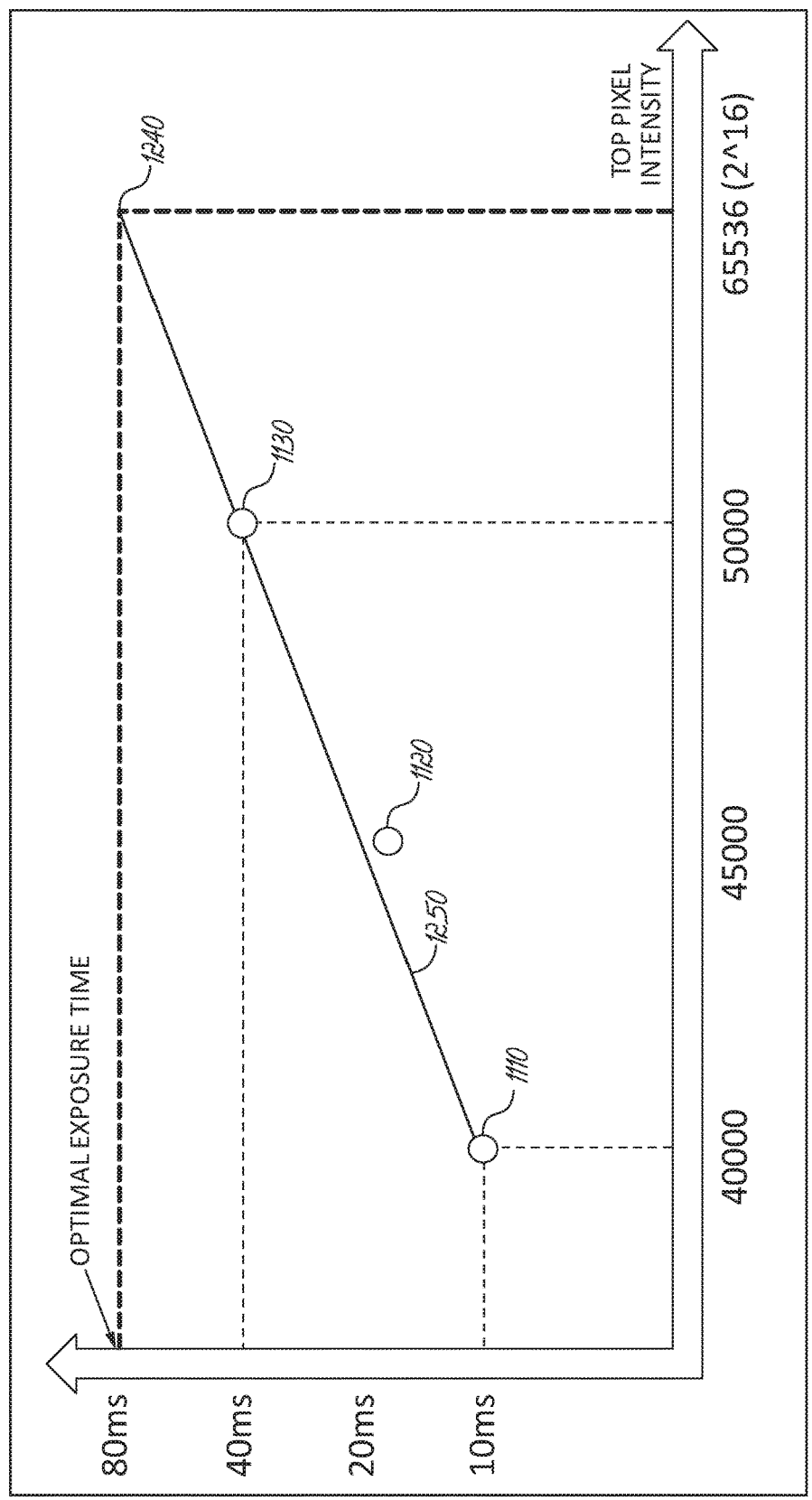
FIG. 12 is an image view of the optimal exposure time that is determined based on the images that have exposure times that have the most separated exposure time durations according to one embodiment of the invention.

In step 840, an optimal exposure time is determined based on one or more of the captured images in the linear relationship. As shown in FIG. 12, after the linear relationship between relationships 1110, 1120, and 1130 is determined to be sufficient, the optimal exposure time is determined based on one or more images in the linear relationship. In an embodiment, the optimal exposure time may be determined from the images that have exposure times that have the most separated exposure time durations. The linear relationship 1250 may be most robustly defined between the images that have exposure times with the most separated exposure time durations. For example, image 910*a* with the exposure time having the shortest exposure time duration in 10 ms as represented by relationship 1110 and image 910*n* with the exposure time having the longest exposure time duration in 40 ms as represented by relationship 1130 may most robustly define the linear relationship 1250 between images 910(*a-n*).

The optimal exposure time may then be determined based on relationship 1110 and relationship 1130 based on the linear relationship 1250 robustly defined between relationship 1110 and relationship 1130. The linear relationship 1250 robustly defined between relationship 1110 and relationship 1130 may then be projected such that the optimal exposure time to obtain an appropriate percentage of pixels that satisfy the pixel intensity saturation level threshold to generate an image for the user to adequately analyze the specimen may be determined.

For example, the linear relationship 1250 robustly defined between relationship 1110 and relationship 1130 is projected to determine relationship 1240. Relationship 1240 represents an optimal exposure time of 80 ms such that a projected image that has the optimal exposure time of 80 ms obtains 65,535 pixels that satisfy the threshold value. Such a projected image with such a significant percentage of pixels that satisfy the threshold value may enable the user to adequately analyze the specimen.

The images that have exposure times with the most separated exposure time durations may then be incorporated to the generation of the projected image at the optimal exposure time. As noted above, the linear relationship 1250 may be most robustly defined between image 910*a* with an exposure time with the shortest exposure time duration of 10 ms and image 910*n* with an exposure time with the longest exposure time duration of 30 ms. Image 910*a* and image 910*n* may then be incorporated to generate the projected image with the optimal exposure time of 80 ms that obtains 65,535 pixels that satisfy the threshold value as represented by relationship 1240. Such a projected image with such a significant percentage of pixels that satisfy the threshold value may enable the user to adequately analyze the specimen.

In an embodiment, the projected image may be generated from a single image included in the images 910(*a-n*). In generating the projected image from the single image, such as image 910*n* as represented by relationship 1130, an optimal exposure time may be determined simply by projecting image 910*n* based on the linear relationship between the images 910(*a-n*). For example, image 910*n* with an exposure time of 40 ms and 50,000 pixels that satisfy the threshold value may be projected based on the linear relationship between the images 910(*a-n*) to generate relationship 1240 with the optimal exposure time of 80 ms and 65,535 pixels that satisfy the threshold value. In an example embodiment, step 840 may be performed by processor 102 of computer system 100 as shown in FIG. 13.

FIG. 13 shows an exemplary computer or computing system 100 that can be used to implement the method and system. The computer system 100 can be a laptop, desktop, server, handheld device (e.g., personal digital assistant (PDA), smartphone, tablet), programmable consumer electronics or programmable industrial electronics.

As illustrated the computer system 100 includes a processor 102 that can be any various available microprocessor (s). For example, the processor can be implemented as dual microprocessors, multi-core and other multiprocessor architectures. The computer system 100 includes memory 104 that can include volatile memory, nonvolatile memory or both. Nonvolatile memory can include read only memory (ROM) for storage of basic routines for transfer of information, such as during computer boot or start-up. Volatile memory can include random access memory (RAM). The computer system 100 can include storage media 106 including, but not limited to, magnetic or optical disk drives, flash memory, and memory sticks.

The computer system 100 can incorporate one or more interfaces, including ports 108 (e.g., serial, parallel, PCM-CIA, USB, FireWire) or interface cards 110 (e.g., sound, video, network, etc.) or the like. In embodiments, an interface supports wired or wireless communications. Input is received from any number of input devices 112 (e.g., keyboard, mouse, joystick, microphone, trackball, stylus, touch screen, scanner, camera, satellite dish, another computer system and the like). The computer system 100 can output data through an output device 114, such as a display (e.g. CRT, LCD, plasma), speakers, printer, another computer or any other suitable output device.

The description above references flowchart illustrations of methods, apparatus (systems) and computer program products. It will be understood that each block of the flowchart illustrations, and combinations of blocks in the flowchart illustrations, and/or part thereof, can be implemented by computer program instructions. These computer program instructions may be loaded onto a computer or other programmable data processing apparatus or otherwise encoded into a logic device to produce a machine, such that the instructions which execute on the computer or other programmable data processing apparatus create means for implementing the functions specified in the flowchart block or blocks. These computer program instructions may also be stored in a computer readable memory that can direct a computer or other programmable data processing apparatus to function in a particular manner, such that the instructions stored in the computer readable memory produce an article of manufacture including instruction means that implement the function specified in the flowchart block or blocks. The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Specific functional blocks, or parts or combinations thereof, presented in relation to the disclosed methods and systems are programmable as separate modules or functional blocks of code. These modules are capable of being stored in a one or multiple-computer storage media in a distributed manner. In one embodiment, these modules are executed to perform the method and system in whole or in part on a single computer. In one embodiment, these modules are executed to perform the disclosed methods and systems on multiple computers that cooperatively execute the modules. In one embodiment, the programs are executed in a virtual environment, where physical hardware operates an abstract layer upon which the disclosed methods and systems are executed in whole or in part across one or more physical hardware platforms.

In addition, it should be understood that the system and method disclosed herein is not limited for use with imaging substrates or objects after electrophoresis, and indeed is also not limited to use in the life sciences field. Instead, the system and method can be used in nearly any imaging system in which it is desired to create a projected image and/or determine an optimal exposure time.

While various aspects in accordance with the principles of the invention have been illustrated by the description of various embodiments, and while the embodiments have been described in considerable detail, they are not intended to restrict or in any way limit the scope of the invention to such detail. The various features shown and described herein may be used alone or in any combination. Additional advantages and modifications will readily appear to those skilled in the art. The invention in its broader aspects is therefore not limited to the specific details and representative devices shown and described. Accordingly, departures may be made from such details without departing from the scope of the general inventive concept.

What is claimed is:

1. A computer implemented method for generating a projected image at an optimal exposure time, comprising:
   capturing a plurality of images with each image captured at a different exposure time;
   assessing each image of the plurality of images and selecting pixels that have intensity values that satisfy an intensity threshold percentage for each image, wherein the intensity threshold percentage is a percentage of pixels included in the image with each pixel included in the percentage of pixels having an intensity value that is higher than an intensity value for each pixel that is excluded from the percentage of pixels;

evaluating whether the intensity values of the selected pixels are distributed above a lower intensity threshold and below an upper intensity threshold;

determining whether a linear relationship exists for the intensity values between each of the captured images for which the intensity values of the selected pixels are above the lower intensity threshold and below the upper intensity threshold, wherein the determining whether the linear relationship exists comprises:

determining a theoretical linear relationship between a first image with a first exposure time duration and a second image with a second exposure time duration, wherein the first exposure time duration is shorter than the second exposure time duration;

projecting the linear relationship to determine an optimal exposure time that has an exposure time duration that exceeds each exposure time duration associated with each of the captured images when the linear relationship exists between each of the captured images, wherein the optimal exposure time is based upon a pixel intensity saturation level threshold; and generating a projected image associated with the optimal exposure time from one or more of the captured images; and determining whether each image that has an exposure time duration that is between the first exposure time duration of the first image and the second exposure time duration of the second image is within a threshold distance of the theoretical linear relationship.

2. The computer implemented method of claim 1, wherein at least three images are captured with each of images captured at different exposure times.

3. The computer implemented method of claim 1, wherein the projecting comprises:

projecting the linear relationship to determine the optimal exposure time when each image that has the exposure time duration that is between the first exposure time duration of the first image and the second exposure time duration of the second image is within the threshold distance of the theoretical linear relationship.

4. The computer implemented method of claim 1, further comprising:

capturing an additional image with an exposure time that has an exposure time duration that exceeds each of the exposure time durations for each of the previously captured images when one or more images that have the exposure time duration that is between the first exposure time duration of the first image and the second exposure time duration of the second image is beyond the threshold distance of the linear relationship.

5. The computer implemented method of claim 4, further comprising:

determining an adjusted theoretical linear relationship between the first image with the first exposure time duration and the one or more additional images with the exposure time duration that exceeds each of the exposure time durations for each of the previously captured images.

6. The computer implemented method of claim 5, further comprising:

determining whether each image that has the exposure time duration that is between the first exposure time duration of the first image and the second exposure time duration of the second image is within the threshold distance of the adjusted theoretical linear relationship.

7. The computer implemented method of claim 6, further comprising:

projecting the adjusted theoretical linear relationship to determine the optimal exposure time when each image that has the exposure time duration that is between the first exposure time duration of the first image and the second exposure time duration of the second image is within the threshold distance of the adjusted theoretical linear relationship.

8. The computer implemented method of claim 7, wherein the first exposure time duration is a shortest time duration of each of the captured images and the second time duration is a longest time duration of each of the captured images.

9. A system for generating a projected image with an optimal exposure time, comprising:

an image capturing device configured to capture a plurality of images with each image captured at a different exposure time;

at least one processor; and a memory coupled with the processor, the memory including instructions that, when executed by the processor cause the processor to:

assess each image of the plurality of images and select pixels that have intensity values that satisfy an intensity threshold percentage for each image, wherein the intensity threshold percentage is a percentage of pixels included in the image with each pixel included in the percentage of pixels having an intensity value that is higher than an intensity value for each pixel that is excluded from the percentage of pixels, evaluate whether the intensity values of the selected pixels are distributed over a lower intensity threshold and below an upper intensity threshold, determine whether a linear relationship exists for the intensity values between each of the captured images for which the intensity values of the selected pixels are above the lower intensity threshold and below the upper intensity threshold between each of the captured images, project the linear relationship to determine an optimal exposure time that has an exposure time duration that exceeds each exposure time duration associated with each of the captured images when the linear relationship exists between each of the captured images, wherein the optimal exposure time is based upon a pixel intensity saturation level threshold, and generate a projected image associated with the optimal exposure time from one or more of the captured images, wherein the instructions when executed by the processor further cause the processor to determine a theoretical linear relationship between a first image with a first exposure time duration and a second image with a second exposure time duration, wherein the first exposure time duration is shorter than the second exposure time duration and wherein the instructions when executed by the processor further cause the processor to determine whether each image that has an exposure time duration that is between the first exposure time duration of the first image and the second exposure time duration of the second image is within a threshold distance of the theoretical linear relationship.

10. The system of claim 9, wherein at least three images are captured with each of the images captured at different exposure times.

11. The system of claim 10, wherein the instructions when executed by the processor further cause the processor to capture an additional image with an exposure time that has an exposure time duration that exceeds each of the exposure time durations for each of the previously captured images when one or more images that have the exposure time duration that is between the first exposure time duration of the first image and the second exposure time duration of the second image is beyond the threshold distance of the linear relationship.

12. The system of claim 11, wherein the instructions when executed by the processor further cause the processor to determine an adjusted theoretical linear relationship between the first image with the first exposure time duration and the additional image with the exposure time duration that exceeds each of the exposure time durations for each of the previously captured images.

13. The system of claim 12, wherein the instructions when executed by the processor further cause the processor determine whether each image that has the exposure time duration that is between the first exposure time duration of the first image and the second exposure time duration of the second image is within the threshold distance of the adjusted theoretical linear relationship.

14. The system of claim 13, wherein the instructions when executed by the processor further cause the processor to project the adjusted theoretical linear relationship to determine the optimal exposure time when each image that has the exposure time duration that is between the first exposure time duration of the first image and the second exposure time duration of the second image is within the threshold distance of the adjusted theoretical linear relationship.

15. The system of claim 14, wherein the first exposure time duration is a shortest time duration of each of the captured images and the second time duration is a longest time duration of each of the captured images.

16. The system of claim 9, wherein the instructions when executed by the processor further cause the processor to project the linear relationship to determine the optimal exposure time when each image that has the exposure time duration that is between the first exposure time duration of the first image and the second exposure time duration of the second image is within the threshold distance of the theoretical linear relationship.

* * * * *